(12) United States Patent
Ohkubo

(10) Patent No.: US 11,174,457 B2
(45) Date of Patent: Nov. 16, 2021

(54) CELL CULTURE APPARATUS

(71) Applicant: Shimadzu Corporation, Kyoto (JP)

(72) Inventor: Tomoki Ohkubo, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 179 days.

(21) Appl. No.: 16/434,867

(22) Filed: Jun. 7, 2019

(65) Prior Publication Data

US 2019/0376015 A1    Dec. 12, 2019

(30) Foreign Application Priority Data

Jun. 8, 2018    (JP) .............................. JP2018-110347

(51) Int. Cl.
  *C12M 1/04*    (2006.01)
  *C12M 1/00*    (2006.01)
  *C12M 1/32*    (2006.01)

(52) U.S. Cl.
  CPC ............ *C12M 23/24* (2013.01); *C12M 23/12* (2013.01); *C12M 23/26* (2013.01); *C12M 29/24* (2013.01)

(58) Field of Classification Search
  CPC ...... C12M 23/12; C12M 23/16; C12M 23/24; C12M 23/26; C12M 23/42; C12M 29/00; C12M 20/02; C12M 29/06; C12M 29/24; C12M 37/04
  See application file for complete search history.

(56) References Cited

U.S. PATENT DOCUMENTS

| | | | | |
|---|---|---|---|---|
| 4,033,825 A | * | 7/1977 | Haddad | C12M 23/48 435/293.2 |
| 5,079,168 A | * | 1/1992 | Amiot | B01D 63/10 435/297.2 |
| 5,416,022 A | * | 5/1995 | Amiot | B01D 63/00 435/297.2 |
| 5,786,215 A | * | 7/1998 | Brown | C12M 23/06 435/297.2 |
| 2017/0355945 A1 | * | 12/2017 | Kamm | C12M 23/16 |
| 2018/0105782 A1 | * | 4/2018 | Redaelli | C12M 23/34 |

OTHER PUBLICATIONS

Chen et al., "High-Throughput Cancer Cell Sphere Formation for Characterizing the Efficacy of Photo Dynamic Therapy in 3D Cell Cultures." Scientific Reports vol. 5, p. 12175, Jul. 8, 2015.

* cited by examiner

*Primary Examiner* — Donald R Spamer
*Assistant Examiner* — Lauren A. Ryan
(74) *Attorney, Agent, or Firm* — Muir Patent Law, PLLC

(57) ABSTRACT

A cell culture apparatus includes a culturing unit having a surface provided with a plurality of concave wells for culturing cells therein, and a flow unit including a gas flow path which allows gas to flow therethrough. The culturing unit includes a gas permeator that is arranged to separate the plurality of wells from the flow unit, the gas permeator having oxygen permeability and liquid impermeability.

11 Claims, 5 Drawing Sheets

MODIFIED EXAMPLE

CELL CULTURE APPARATUS

CROSS-REFERENCE TO RELATED APPLICATIONS

This application claims the benefit of priority to Japanese Patent Application No. 2018-110347 filed on Jun. 8, 2018. The entire contents of this application are hereby incorporated herein by reference.

BACKGROUND OF THE INVENTION

Field of the Invention

The present invention relates to a cell culture apparatus, and more particularly, it relates to a cell culture apparatus including a culturing unit having a surface provided with a plurality of concave wells in which cells are cultured.

Description of the Background Art

A cell culture apparatus including a culturing unit having a surface provided with a plurality of concave wells in which cells are cultured is known in general. Such a cell culture apparatus is disclosed in Y. C. Chen, et al., "High-Throughput Cancer Cell Sphere Formation for Characterizing the Efficacy of Photo Dynamic Therapy in 3D Cell Cultures", SCIENTIFIC REPORTS vol. 5, p. 12175, Jul. 8, 2015, for example.

A cell culture apparatus disclosed in Y. C. Chen, et al., "High-Throughput Cancer Cell Sphere Formation for Characterizing the Efficacy of Photo Dynamic Therapy in 3D Cell Cultures", SCIENTIFIC REPORTS vol. 5, p. 12175, Jul. 8, 2015 has a surface provided with a plurality of concave wells in which cells are cultured. In each of the plurality of wells, a cellular mass is contained (seeded). The cell contained (seeded) in each of the plurality of wells is cultured with a culture solution that flows in via a flow path connected to the well. The cell contained (seeded) in each of the plurality of wells can take in oxygen dissolved in the culture solution at the time of culture. Furthermore, each of the plurality of wells is exposed to outside air, and oxygen can be taken in from the air. In addition, the cell takes in oxygen to discharge carbon dioxide (exchange oxygen for carbon dioxide).

SUMMARY OF THE INVENTION

However, in a conventional cell culture apparatus as disclosed in Y. C. Chen, et al., "High-Throughput Cancer Cell Sphere Formation for Characterizing the Efficacy of Photo Dynamic Therapy in 3D Cell Cultures", SCIENTIFIC REPORTS vol. 5, p. 12175, Jul. 8, 2015, it is difficult for cells to take in oxygen from air when a space around the cell culture apparatus (wells) is small (or the air is difficult to flow) and the amount of oxygen around the wells is relatively small, for example. In this case, the cells contained (seeded) in the wells can take in oxygen only from a culture solution, and thus it is conceivably difficult to supply a sufficient amount of oxygen to the cells contained (seeded) in the wells (the rate of exchange of oxygen for carbon dioxide by the cells is conceivably insufficient). In such a case, there is a problem that it becomes difficult to properly culture the cells contained (seeded) in the wells.

The present invention has been proposed in order to solve the aforementioned problems, and an object of the present invention is to provide a cell culture apparatus capable of properly culturing cells contained (seeded) in wells by supplying a sufficient amount of oxygen to the cells.

In order to attain the aforementioned object, a cell culture apparatus according to an aspect of the present invention includes a culturing unit having a surface provided with a plurality of concave wells for culturing cells therein, and a flow unit provided on at least one of one side and the other side of the culturing unit in a direction orthogonal to the surface of the culturing unit, the flow unit including a gas flow path which allows gas to flow therethrough. The culturing unit includes a gas permeator that is arranged to separate the plurality of wells of the culturing unit from the flow unit, the gas permeator having oxygen permeability and liquid impermeability.

In the cell culture apparatus according to this aspect of the present invention, as described above, the flow unit including the gas flow path is separated from the plurality of wells by the gas permeator such that the gas (including oxygen) can flow to the wells via the gas flow path. Accordingly, the oxygen in the gas that flows through the gas flow path is transmitted through the gas permeator such that the oxygen is supplied to the cells contained (seeded) in the wells. Consequently, even when the amount of oxygen is relatively small in a space around the wells (other than the flow unit), a sufficient amount of oxygen can be supplied to the cells contained (seeded) in the wells via the flow unit. Thus, the cells contained (seeded) in the wells can be appropriately cultured.

Furthermore, in order to increase the amount of oxygen supplied to the cells, it is not necessary to increase the amount of culture solution in which oxygen is dissolved. Thus, collapse of a mass of the cells in the wells caused by the flow of the increased amount of culture solution can be significantly reduced or prevented.

In the aforementioned cell culture apparatus according to this aspect, the culturing unit is preferably flexible and circumferentially windable, the flow unit is preferably flexible and circumferentially windable integrally with the culturing unit, and the gas permeator is preferably arranged to separate each of the plurality of wells provided on at least one of an inner circumferential surface and an outer circumferential surface of the culturing unit from the flow unit in a state in which the culturing unit and the flow unit are integrally wound. The culturing unit is circumferentially wound, and thus it is difficult for oxygen to reach the inner circumferential portion. Therefore, including the flow unit is particularly effective for supplying oxygen to the culturing unit circumferentially wound.

In such a case, the flow unit preferably further includes a plurality of pillars that extend in a radial direction between a surface of the gas flow path on an inner circumferential side and a surface of the gas flow path on an outer circumferential side in the state in which the culturing unit and the flow unit are integrally wound. According to this structure, the plurality of pillars can support the surface of the gas flow path on the inner circumferential side and the surface of the gas flow path on the outer circumferential side, and thus collapse (blocking) of the gas flow path (flow unit) can be significantly reduced or prevented.

In the aforementioned cell culture apparatus in which the flow unit includes the plurality of pillars, each of the plurality of pillars preferably has a non-overlapping portion with the wells as viewed in the radial direction in the state in which the culturing unit and the flow unit are integrally wound. According to this structure, as compared with the case in which the whole of each of the pillars overlaps the wells as viewed in the radial direction, an area in which the gas flow path and the wells overlap each other in the radial direction via the gas permeator can be increased. Consequently, oxygen can be more efficiently supplied to the cells contained (seeded) in the wells via the gas flow path. Moreover, hindrance, by the pillars, of discharge of carbon dioxide from the cells in the wells to the gas flow path can be significantly reduced or prevented.

In such a case, each of the pillars preferably has a center located substantially at a midpoint between the adjacent wells, as viewed in the radial direction. According to this structure, the center of each of the pillars can be disposed in a portion (a portion in which the wells are not provided) between the adjacent wells. Consequently, an area in which the pillars and the wells overlap each other in the radial direction can be easily decreased.

In the aforementioned cell culture apparatus in which each of the pillars has the non-overlapping portion with the wells, the plurality of wells are preferably provided in a staggered manner on at least one of the inner circumferential surface and the outer circumferential surface of the culturing unit, and the plurality of pillars are preferably provided in a staggered manner inside the gas flow path such that each of the plurality of pillars has a non-overlapping portion with the wells. According to this structure, both the wells and the pillars are provided in a staggered manner, and thus the wells and the pillars can be densely disposed as compared with the case in which the wells and the pillars are disposed in a matrix. Consequently, the number of each of the wells and the pillars per unit area can be increased. The term "staggered manner" indicates a state in which wells in adjacent rows are offset from each other in a predetermined direction when a plurality of rows of the wells arrayed along the predetermined direction are disposed side by side so as to be adjacent to each other along a direction orthogonal to the predetermined direction.

Furthermore, both the wells and the pillars are provided in a staggered manner, and thus each of the plurality of pillars can easily overlap a portion between the adjacent wells (a portion in which the wells are not provided) in the radial direction. Consequently, the area in which the pillars and the wells overlap each other in the radial direction can be effectively decreased.

In the aforementioned cell culture apparatus in which each of the pillars has the non-overlapping portion with the wells, each of the plurality of wells preferably has a substantially cylindrical concave shape, each of the plurality of pillars preferably has a substantially cylindrical shape, and a diameter of each of the pillars having the substantially cylindrical shape is preferably equal to or less than a diameter of each of the wells having the substantially cylindrical concave shape. According to this structure, as compared with the case in which the diameter of each of the pillars is larger than the diameter of each of the wells, the area in which the plurality of pillars and the plurality of wells overlap each other in the radial direction can be further decreased.

In the aforementioned cell culture apparatus according to this aspect, the flow unit preferably has a substantially rectangular shape, and the gas flow path preferably has an inlet provided in a side surface that extends along a short-side direction of the flow unit at an end of the flow unit on an outer diameter side in a state in which the culturing unit and the flow unit are integrally wound. According to this structure, the gas introduced from the inlet provided in the side surface that extends along the short-side direction of the flow unit flows along the longitudinal direction of the flow unit such that the gas can flow through the entire flow unit. Consequently, as compared with the case in which the inlet is provided in the side surface in the longitudinal direction of the flow unit, the gas can flow through the entire flow unit while an increase in the size of the inlet is significantly reduced or prevented. Thus, the inlet can be relatively easily formed.

In this case, the apparatus is preferably configured to allow the gas supplied from a pump to flow into the inlet of the gas flow path. According to this structure, the pump can introduce the gas into the gas flow path while applying pressure to the gas. Consequently, stagnation of the flow of the gas can be significantly reduced or prevented in the gas flow path.

In the aforementioned cell culture apparatus according to this aspect, each of the culturing unit, the flow unit, and the gas permeator is preferably made of silicone rubber. Silicone rubber has a high biocompatibility, and thus when the culturing unit is silicone rubber, the cells can be more appropriately cultured. Moreover, each of the culturing unit, the flow unit, and the gas permeator is made of the same material such that an increase in types of components can be significantly reduced or prevented.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.

The structure of a cell culture apparatus 100 according to this embodiment is now described with reference to FIGS. 1 to 8.

The cell culture apparatus 100 is used for research in the field of drug discovery and biology, for example, and is expected to be applied to the field of regenerative medicine etc. Specifically, the cell culture apparatus 100 is applied to differentiation induction of pluripotent stem cell-derived tissues for transplantation therapy, expansion of pluripotent stem cells for transplantation therapy, differentiation induction of pluripotent stem cell-derived tissues for drug screening, etc.

(Structure of Cell Culture Apparatus)

Figure 1:
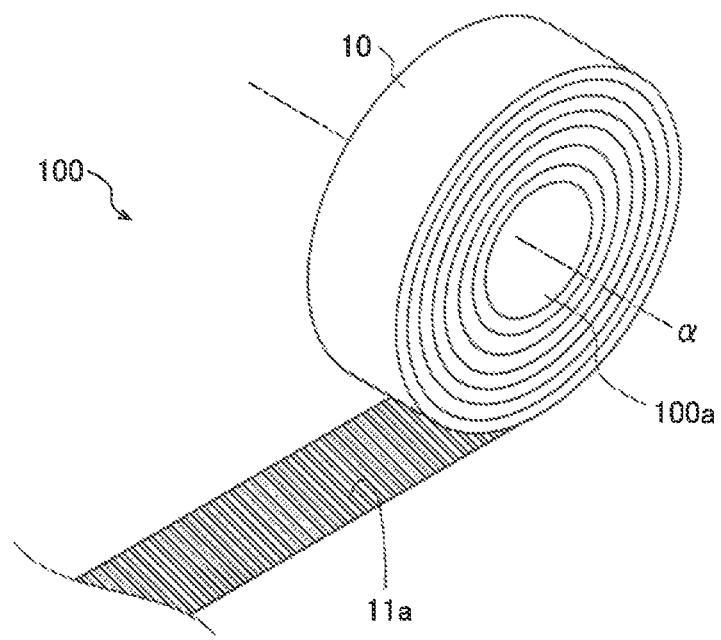
FIG. 1 is a perspective view showing the structure of a (microarray) tape of a cell culture apparatus according to an embodiment.

As shown in FIG. 1, the cell culture apparatus 100 includes a microarray tape (hereinafter simply referred to as a tape 10) that can be circumferentially wound. The tape 10 is wound about the central axis α of the winding. The tape 10 is wound around a core 100a.

Figure 2:
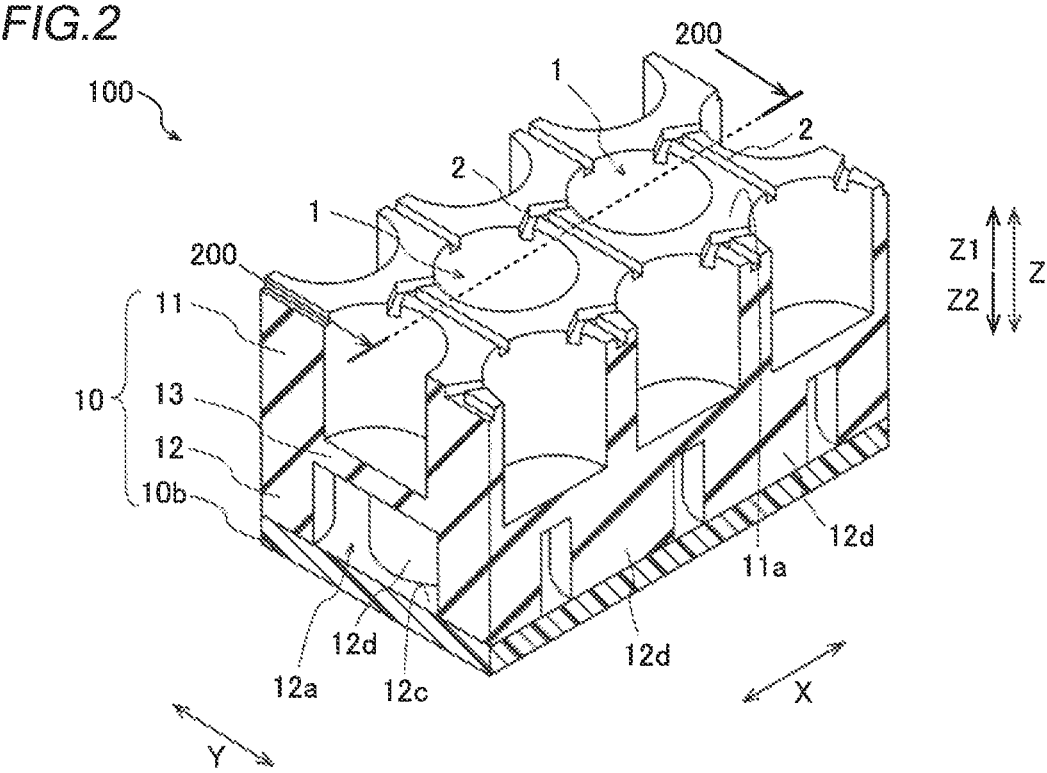
FIG. 2 is a sectional perspective view showing the structure of the (microarray) tape of the cell culture apparatus according to the embodiment.

As shown in FIG. 2, the cell culture apparatus 100 includes a culturing unit 11 and a flow unit 12 that constitute the tape 10. The culturing unit 11 includes a gas permeator 13. The tape 10 (the culturing unit 11, the flow unit 12, and the gas permeator 13) has a substantially rectangular shape in a state in which the tape 10 is not circumferentially wound.

The culturing unit 11 is flexible and can be circumferentially wound. In addition, on the inner circumferential surface 11a of the culturing unit 11, a plurality of wells 1 in which cells 101 (see FIG. 3) are cultured are provided. The cells 101 are, for example, induced pluripotent stem (IPS) cells or embryonic stem (ES) cells. The inner circumferential surface 11a is an example of a "surface" in the claims.

Each of the plurality of wells 1 has a concave shape, and the cells 101 are contained (seeded) in the wells. Specifically, the wells 1 each have a substantially cylindrical concave shape.

The plurality of wells 1 have the same structure (size). Specifically, the diameter of each of the substantially cylindrical concave wells 1 has a length L1 (see FIG. 5). The length L1 is about several hundreds of μm, for example.

The inner circumferential surface 11a of the culturing unit 11 provided with the plurality of wells 1 is non-adherent to the cells 101. Specifically, the inner circumferential surface 11a of the culturing unit 11 is coated with a non-adherent polymer to the cells 101. Thus, the cells 101 are unlikely to be adsorbed to the inner circumferential surface 11a, and thus the cells 101 adhere (or are adsorbed) to each other. Consequently, a mass of the cells 101 is formed in each of the wells 1.

A culture solution flow path 2 connected to each of the plurality of wells 1 is provided on the inner circumferential surface 11a of the culturing unit 11. A culture solution flows through the culture solution flow path 2 such that the culture solution is introduced into each of the plurality of wells 1.

The plurality of wells 1 and a plurality of culture solution flow paths 2 are covered by the outer circumferential surface 10a (see FIG. 3) of the tape 10 wound on the inner circumferential side of the plurality of wells 1 and the plurality of culture solution flow paths 2 in a state in which the tape 10 is circumferentially wound.

The flow unit 12 is flexible and can be circumferentially wound. Specifically, the flow unit 12 can be circumferentially wound integrally with the culturing unit 11. The flow unit 12 is provided on the outer circumferential side of the culturing unit 11.

The tape 10 includes a plastic film 10b provided on the outer circumferential side of the flow unit 12. The plastic film 10b can be wound integrally with the culturing unit 11 and the flow unit 12.

The gas permeator 13 is oxygen permeable and liquid impermeable. The gas permeator 13 separates the plurality of wells 1 of the culturing unit 11 from the flow unit 12. In addition, the gas permeator 13 also transmits carbon dioxide.

Figure 3:
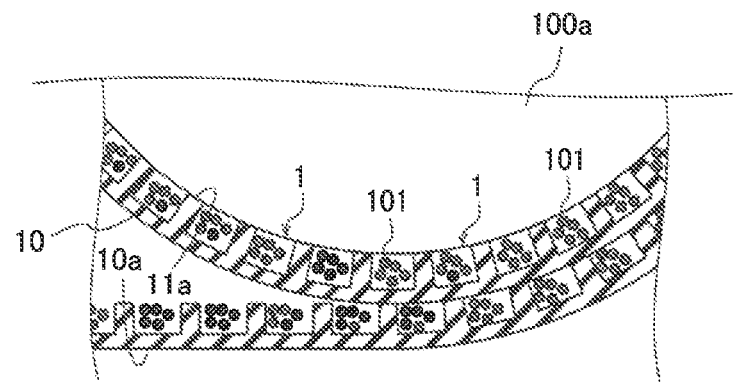
FIG. 3 is an enlarged sectional view showing the structure of the (microarray) tape of the cell culture apparatus according to the embodiment.
Figure 4:
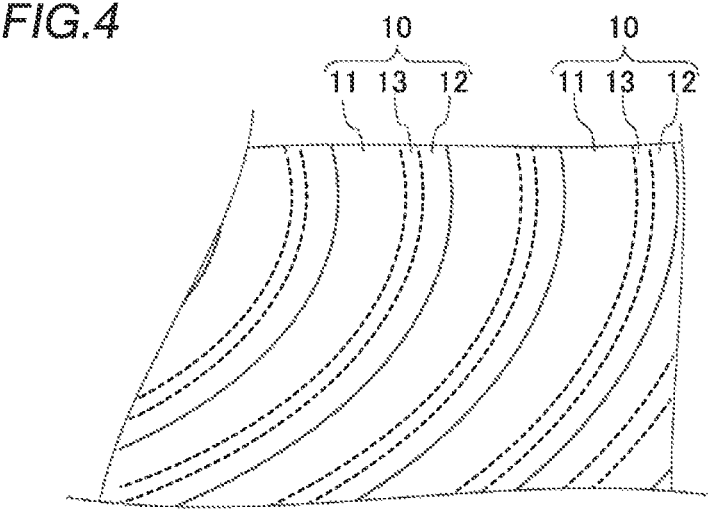
FIG. 4 is an enlarged perspective view showing the structure of the (microarray) tape of the cell culture apparatus according to the embodiment.

Specifically, in a state in which the culturing unit 11 and the flow unit 12 are integrally wound, the gas permeator 13 separates each of the plurality of wells 1 provided on the inner circumferential surface 11a of the culturing unit 11 from the flow unit 12. That is, the gas permeator 13 is circumferentially wound integrally with the culturing unit 11 and the flow unit 12 (see FIG. 4). In FIG. 3, illustration of the plastic film 10b is omitted for simplification.

The culturing unit 11, the flow unit 12, and the gas permeator 13 are integral and unitary with each other. Specifically, each of the culturing unit 11, the flow unit 12, and the gas permeator 13 is made of silicone rubber.

In this embodiment, air flows through the flow unit 12. In the cell culture apparatus 100, the air (oxygen contained in the air) that flows through the flow unit 12 is supplied to each of the plurality of wells 1 of the culturing unit 11. The air is an example of a "gas" in the claims.

Specifically, the flow unit 12 includes a gas flow path 12a through which air flows. Oxygen contained in the air that flows through the gas flow path 12a is transmitted (by molecular diffusion) through the gas permeator 13 and flows into the wells 1. Thus, the oxygen is supplied to the cells 101 contained (seeded) in the wells 1. In addition, the cells 101 take in oxygen to discharge carbon dioxide. The carbon dioxide discharged from the cells 101 of the wells 1 is transmitted through the gas permeator 13 and flows out (diffuses) to the gas flow path 12a.

Figure 5:
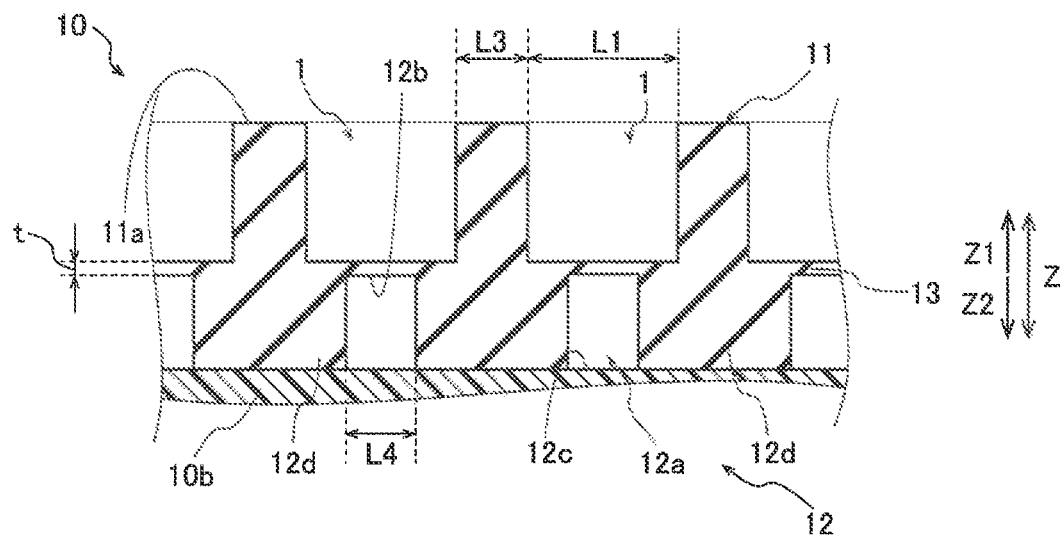
FIG. 5 is a sectional view taken along the line 200-200 in FIG. 2.

In this embodiment, as shown in FIG. 5, the flow unit 12 includes a plurality of pillars 12d that extend in a radial direction (a Z direction in FIG. 5) between a surface 12b of the gas flow path 12a on the inner circumferential side and a surface 12c of the gas flow path 12a on the outer circumferential side.

In FIG. 5, illustration of the culture solution flow path 2 is omitted for simplification. The radial direction is an example of a "direction orthogonal to the surface" in the claims. In addition, the pillars 12d may be inclined with respect to the radial direction and extend.

Figure 6:
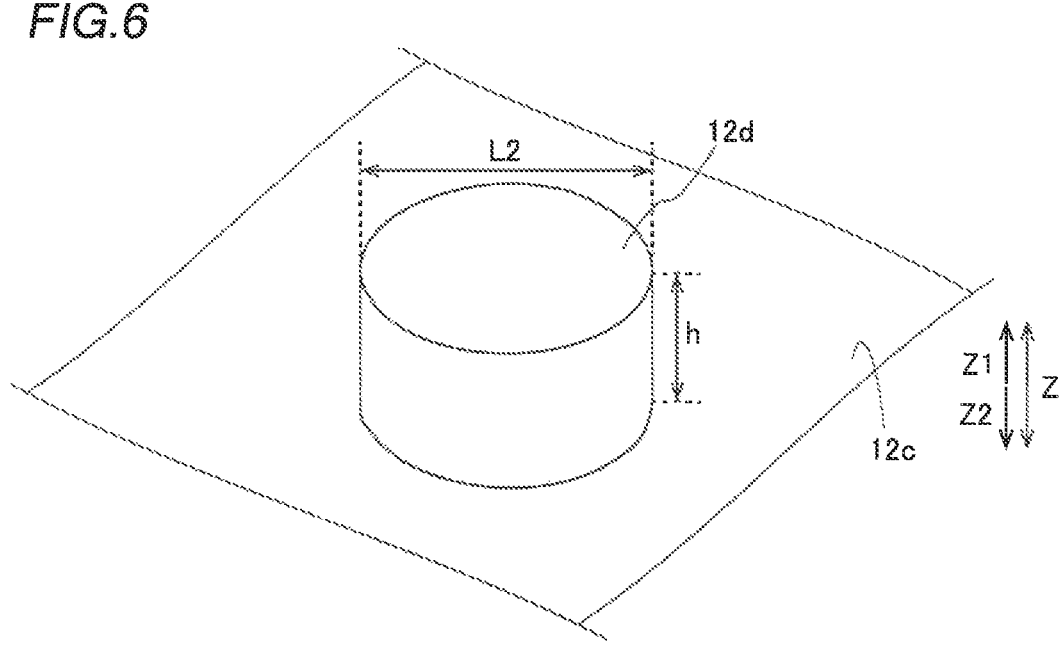
FIG. 6 is a diagram showing the structure of a pillar of a flow unit according to the embodiment.

Specifically, as shown in FIG. 6, each of the plurality of pillars 12d has a substantially cylindrical shape. The diameter of each of the pillars 12d has a length L2. The length L2 is about several hundreds of μm, for example. In addition, each of the pillars 12d has a height h in the Z direction. The height h is, for example, about several hundreds of μm. The length L2 of each of the pillars 12d is larger than the height h.

The gas permeator 13 has a thickness t (see FIG. 5) in the Z direction. The thickness t is, for example, about several tens of μm. The thickness t of the gas permeator 13 is smaller than the height h of each of the pillars 12d.

In this embodiment, the diameter (length L2) of each of the substantially cylindrical pillars 12d is substantially equal to the diameter (length L1) of each of the substantially cylindrical concave wells 1. A spacing between adjacent wells 1 has a length L3 (see FIG. 5). The length L3 is, for example, about several tens of μm to about 100 μm. That is, the length L3 of the spacing between the adjacent wells 1 is smaller than each of the length L1 of the diameter of each of the wells 1 and the length L2 of the diameter of each of the pillars 12d. Furthermore, a spacing between adjacent pillars 12d has a length L4. The length L4 is substantially equal to the length L3 of the spacing between the adjacent wells 1.

Figure 7:
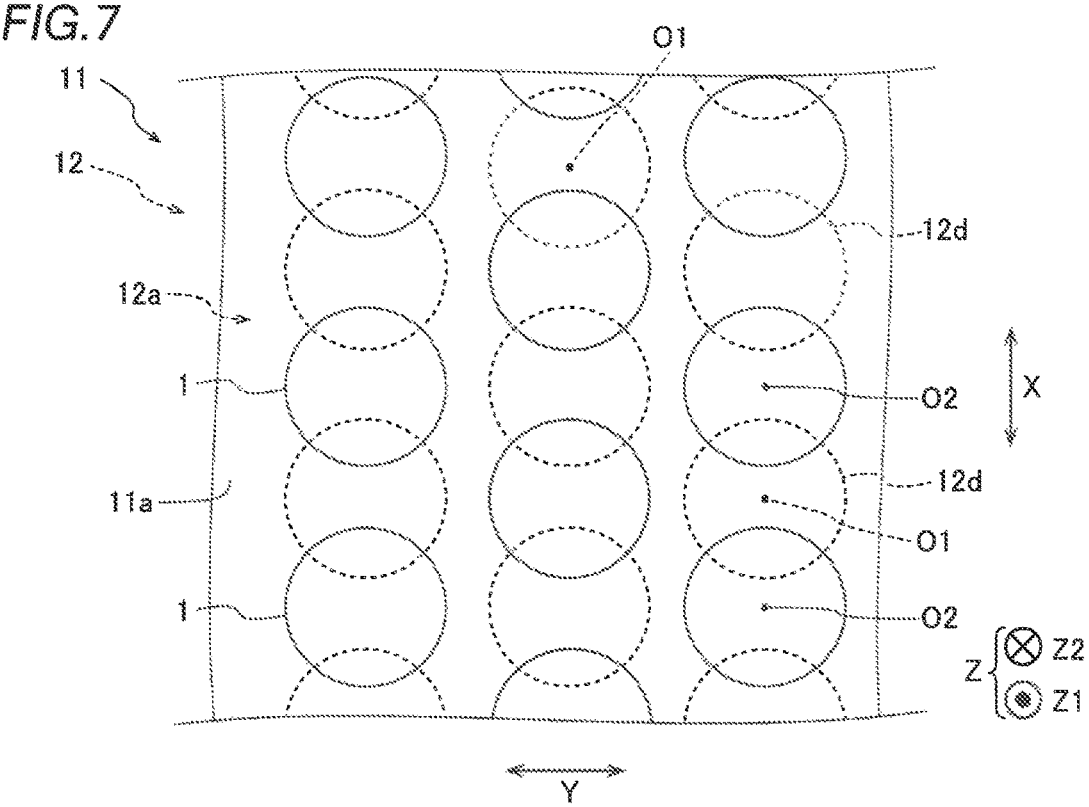
FIG. 7 is a diagram illustrating the arrangement relationship between wells and pillars of the cell culture apparatus according to the embodiment.

As shown in FIG. 7, the plurality of wells 1 are provided in a staggered manner on the inner circumferential surface 11a of the culturing unit 11. Furthermore, the plurality of pillars 12d are provided in a staggered manner inside the gas flow path 12a such that a portion of each of the pillars 12d does not overlap the wells 1. That is, the arrangement relationship between the plurality of wells 1 is substantially the same as the arrangement relationship between the plurality of pillars 12d.

In a state in which the culturing unit 11 and the flow unit 12 are integrally wound, a portion of each of the plurality of pillars 12d (shown by dashed circles in FIG. 7) does not overlap the wells 1 (shown by solid circles in FIG. 7) as viewed in the radial direction (from the Z1 direction side). In other words, each of the plurality of pillars 12d partially overlaps the wells 1.

Specifically, as viewed in the radial direction (from the Z1 direction side), the center O1 of each of the pillars 12d is located approximately at a center between the centers O2 of the wells 1 adjacent to each other. More specifically, the center O1 of each of the pillars 12d is located approximately at a center between the centers O2 of the wells 1 adjacent to each other along the longitudinal direction (an X direction in FIG. 7) of the culturing unit 11. As viewed in the radial direction (from the Z1 direction side), both ends (and the vicinities of both the ends) of each of the pillars 12d in the X direction overlap the wells 1. Furthermore, as viewed in the radial direction (from the Z1 direction side), portions of the wells 1 that do not overlap the pillars 12d overlap the gas flow path 12a through which air flows.

Figure 8:
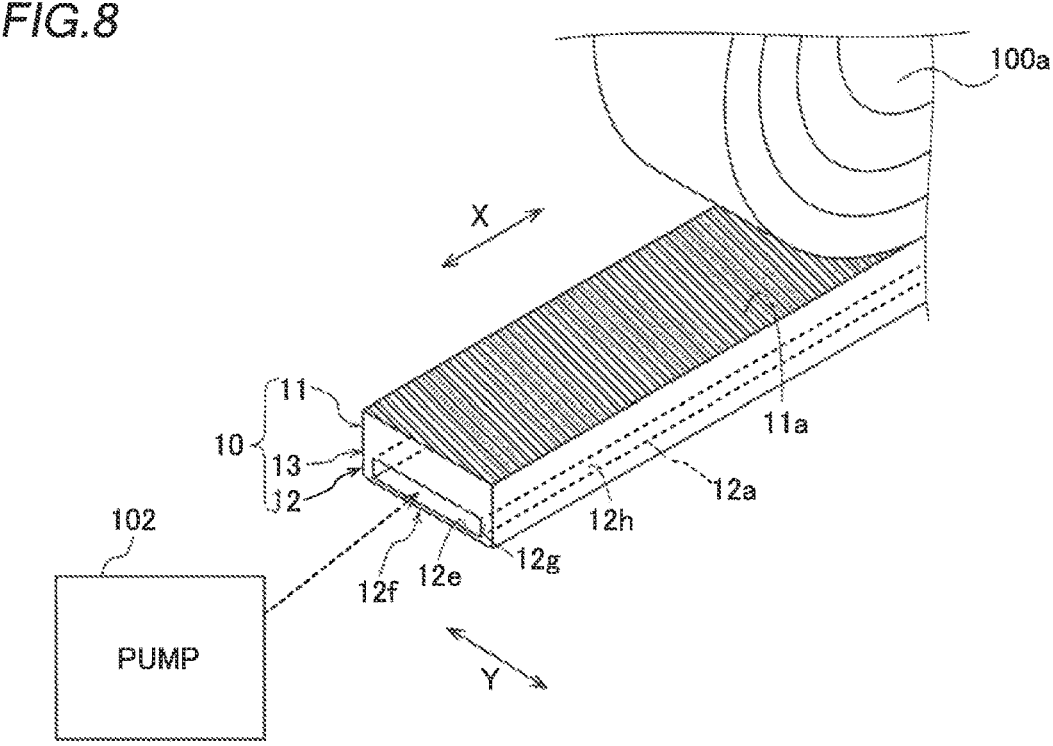
FIG. 8 is a diagram illustrating a method for introducing air into the flow unit of the cell culture apparatus according to the embodiment.

In this embodiment, as shown in FIG. 8, an inlet 12e of the gas flow path 12a is provided at an end 12f of the flow unit 12 on the outer diameter side in a state in which the culturing unit 11 and the gas flow path 12 are integrally wound. Specifically, the inlet 12e is provided in a side surface 12g that extends along the short-side direction (a Y direction in FIG. 8) of the flow unit 12 at the end 12f. Furthermore, only one inlet 12e of the gas flow path 12a is provided in the side surface 12g. The inlet 12e has a substantially rectangular shape, the long side of which extends along the Y direction. The Y direction is an example of a "short-side direction" in the claims.

Although illustration is omitted, the gas flow path 12a includes an outlet at an end on the opposite side to the end 12f. Air introduced from the inlet 12e and flowing through the gas flow path 12a is discharged from the outlet. Thus, the air is circulated through the gas flow path 12a. In a side surface 12h that extends along the longitudinal direction (the X direction in FIG. 8) of the gas path portion 12, an opening or the like through which air flows in and out is not provided.

Air supplied from a pump 102 flows into the inlet 12e of the gas flow path 12a. Specifically, the pump 102 and the inlet 12e are connected to each other by a pipe (not shown), and air is sent from the pump 102 to the inlet 12e via the pipe. The culture solution flows in the Y direction through the culture solution flow path 2 (see FIG. 2), whereas the air flows in the X direction (orthogonal to the Y direction) through the gas flow path 12a. In addition, gas (suitable for cultivation of the cells 101) other than air may be supplied from the pump 102.

(Advantages Derived from this Embodiment)

According to this embodiment, the following advantages are obtained.

According to this embodiment, as described above, the cell culture apparatus 100 includes the culturing unit 11 having the inner circumferential surface 11a provided with the plurality of concave wells 1 in which the cells 101 are cultured, and the flow unit 12 provided on the outer circumferential side of the culturing unit 11 and including the gas flow path 12a through which gas flows. Furthermore, the culturing unit 11 includes the gas permeator 13 that separates the plurality of wells 1 of the culturing unit 11 from the flow unit 12 and is oxygen permeable and liquid impermeable. Accordingly, the oxygen in the air that flows through the flow unit 12 is transmitted through the gas permeator 13 such that the oxygen is supplied to the cells 101 contained (seeded) in the wells 1. Consequently, even when the amount of oxygen is relatively small in the space around the wells 1 (other than the flow unit 12), a sufficient amount of oxygen can be supplied to the cells 101 contained (seeded) in the wells 1 via the flow unit 12 (insufficiency of the rate of exchange of oxygen for carbon dioxide by the cells 101 can be significantly reduced or prevented). Thus, the cells 101 contained (seeded) in the wells 1 can be appropriately cultured.

Furthermore, in order to increase the amount of oxygen supplied to the cells 101, it is not necessary to increase the amount of culture solution in which oxygen is dissolved. Thus, collapse of the mass of the cells 101 in the wells 1 caused by the flow of the increased amount of culture solution can be significantly reduced or prevented.

According to this embodiment, as described above, in the cell culture apparatus 100, the gas permeator 13 separates each of the plurality of wells 1 provided on the inner circumferential surface 11a of the culturing unit 11 from the flow unit 12 in a state in which the culturing unit 11 and the flow unit 12 are integrally wound. The culturing unit 11 is circumferentially wound, and thus it is difficult for oxygen to reach the inner circumferential portion. Therefore, including the flow unit 12 is particularly effective for supplying oxygen to the culturing unit 11 circumferentially wound.

According to this embodiment, as described above, in the cell culture apparatus 100, the flow unit 12 includes the gas flow path 12a through which air flows and the plurality of pillars 12d that extend in the radial direction between the surface 12b of the gas flow path 12a on the inner circumferential side and the surface 12c of the gas flow path 12a on the outer circumferential side in a state in which the culturing unit 11 and the flow unit 12 are integrally wound. Accordingly, the plurality of pillars 12d can support the surface 12b of the gas flow path 12a on the inner circumferential side and the surface 12c of the gas flow path 12a on the outer circumferential side, and thus collapse (blocking) of the gas flow path 12a (flow unit 12) can be significantly reduced or prevented.

According to this embodiment, as described above, in the cell culture apparatus 100, a portion of each of the plurality of pillars 12d does not overlap the wells 1 as viewed in the radial direction in a state in which the culturing unit 11 and the flow unit 12 are integrally wound. Accordingly, as compared with the case in which the whole of each of the pillars 12d overlaps the wells 1 as viewed in the radial direction, an area in which the gas flow path 12a and the wells 1 overlap each other in the radial direction via the gas permeator 13 can be increased. Consequently, oxygen can be more efficiently supplied to the cells 101 contained (seeded) in the wells 1 via the gas flow path 12a. Moreover, hindrance, by the pillars 12d, of discharge of carbon dioxide from the cells 101 in the wells 1 to the gas flow path 12a can be significantly reduced or prevented.

According to this embodiment, as described above, in the cell culture apparatus 100, the center O1 of each of the pillars 12d is located approximately at the center between the centers O2 of the wells 1 adjacent to each other, as viewed in the radial direction. Accordingly, the center O1 of each of the pillars 12d can be disposed in a portion (a portion in which the wells 1 are not provided) between the wells 1 adjacent to each other. Consequently, an area in which the pillars 12d and the wells 1 overlap each other in the radial direction can be easily decreased.

According to this embodiment, as described above, in the cell culture apparatus 100, the plurality of wells 1 are provided in a staggered manner on the inner circumferential surface 11a of the culturing unit 11, and the plurality of pillars 12d are provided in a staggered manner inside the gas flow path 12a such that a portion of each of the plurality of pillars 12d does not overlap the wells 1. Accordingly, both the wells 1 and the pillars 12d are provided in a staggered manner, and thus the wells 1 and the pillars 12d can be densely disposed as compared with the case in which the wells 1 and the pillars 12d are disposed in a matrix. Consequently, the number of each of the wells 1 and the pillars 12d per unit area can be increased.

Furthermore, both the wells 1 and the pillars 12d are provided in a staggered manner, and thus each of the plurality of pillars 12d can easily overlap a portion between the wells 1 adjacent to each other (a portion in which the wells 1 are not provided) in the radial direction. Consequently, the area in which the pillars 12d and the wells 1 overlap each other in the radial direction can be effectively decreased.

According to this embodiment, as described above, in the cell culture apparatus 100, the diameter of each of the substantially cylindrical pillars 12d is equal to or less than the diameter of each of the substantially cylindrical concave wells 1. Accordingly, as compared with the case in which the diameter of each of the pillars 12d is larger than the diameter of each of the wells 1, the area in which the plurality of pillars 12d and the plurality of wells 1 overlap each other in the radial direction can be further decreased.

According to this embodiment, as described above, in the cell culture apparatus 100, the inlet 12e of the gas flow path 12a is provided in the side surface 12g that extends along the short-side direction of the flow unit 12 at the end 12f of the flow unit 12 on the outer diameter side in a state in which the culturing unit 11 and the flow unit 12 are integrally wound. Accordingly, the air introduced from the inlet 12e provided in the side surface 12g that extends along the short-side direction of the flow unit 12 flows along the longitudinal direction of the flow unit 12 such that the air can flow through the entire flow unit 12. Consequently, as compared with the case in which the inlet 12e is provided in the side surface 12h in the longitudinal direction of the flow unit 12, the air can flow through the entire flow unit 12 while an increase in the size of the inlet 12e is significantly reduced or prevented. Thus, the inlet 12e can be relatively easily formed.

According to this embodiment, as described above, in the cell culture apparatus 100, each of the culturing unit 11, the flow unit 12, and the gas permeator 13 is made of silicone rubber. Silicone rubber has a high biocompatibility, and thus when the culturing unit 11 is silicone rubber, the cells 101 can be more appropriately cultured. Moreover, each of the culturing unit 11, the flow unit 12, and the gas permeator 13 is made of the same material such that an increase in types of components can be significantly reduced or prevented. In addition, silicone rubber is flexible, and thus when each of the culturing unit 11, the flow unit 12, and the gas permeator 13 is made of silicone rubber, the culturing unit 11, the flow unit 12, and the gas permeator 13 can be easily circumferentially wound.

(Modified Examples)

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the flow unit 12 is provided on the outer circumferential side of the culturing unit 11 in the aforementioned embodiment, the present invention is not limited to this. For example, the flow unit 12 may be provided on the inner circumferential side of the culturing unit 11.

Figure 9:
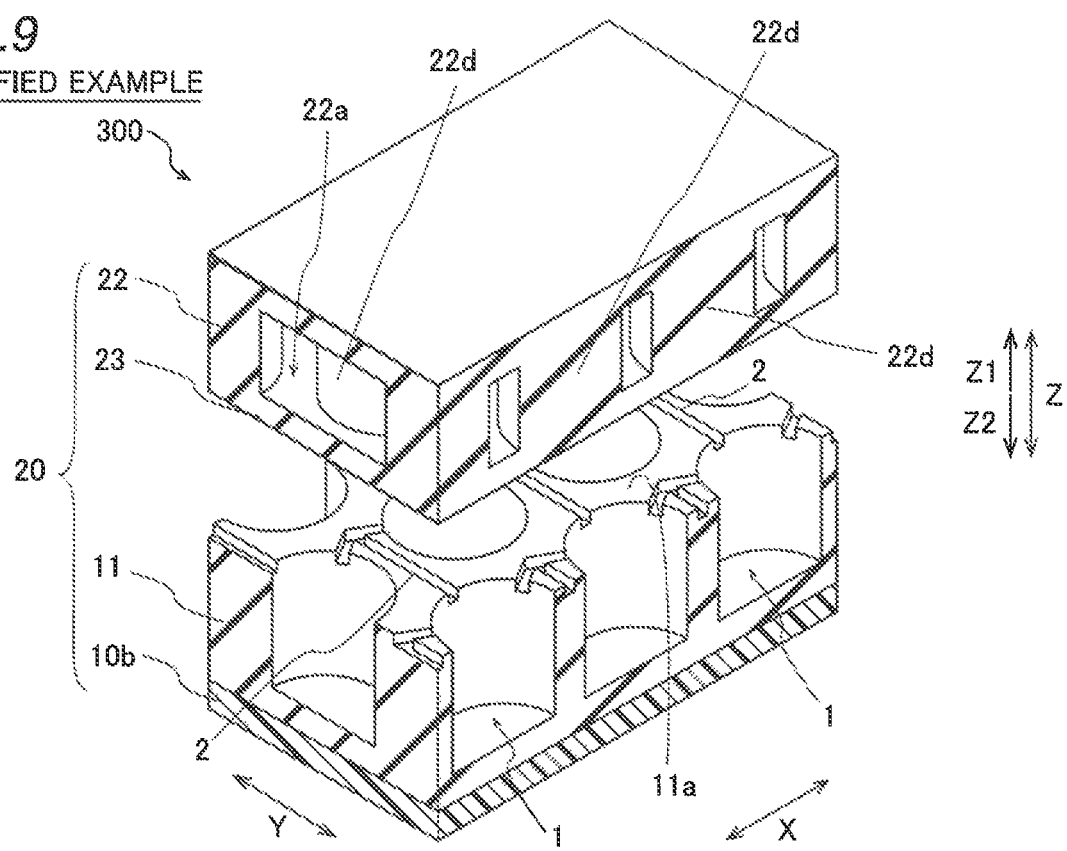
FIG. 9 is a sectional perspective view showing the structure of a (microarray) tape of a cell culture apparatus according to a modified example of the embodiment.

Specifically, as shown in FIG. 9, a cell culture apparatus 300 includes a culturing unit 11, a flow unit 22, and a gas permeator 23 that constitute a tape 20. The flow unit 22 is wound integrally with the culturing unit 11 on the inner circumferential side of the culturing unit 11. The gas permeator 23 separates each of a plurality of wells 1 provided on the inner circumferential surface 11a (surface, circumferential surface) of the culturing unit 11 from the flow unit 22 in a state in which the culturing unit 11 and the flow unit 22 are integrally wound. The flow unit 22 and the gas permeator 23 are integral and unitary with each other. Moreover, the flow unit 22 and the gas permeator 23 are separate from the culturing unit 11.

Furthermore, the flow unit 22 includes a gas flow path 22a through which air flows and a plurality of pillars 22d that extend in a radial direction (a Z direction in FIG. 9) inside the gas flow path 22a.

Furthermore, each of the flow unit 22 and the gas permeator 23 is made of silicone rubber.

While the flow unit 12 is provided only on the outer circumferential side of the culturing unit 11 in the aforementioned embodiment, the present invention is not limited to this. For example, the flow unit 12 may be provided on both the inner circumferential side and the outer circumferential side of the culturing unit 11.

While a portion of each of the plurality of pillars 12d does not overlap the wells 1 in the aforementioned embodiment, the present invention is not limited to this. For example, the whole of each of the plurality of pillars 12d may not overlap the wells 1.

While the plurality of wells 1 are disposed in a staggered pattern, and the plurality of pillars 12d are also disposed in a staggered pattern in the aforementioned embodiment, the present invention is not limited to this. For example, the plurality of wells 1 may be disposed in a matrix, and the plurality of pillars 12d may also be disposed in a matrix. The term "matrix" indicates an arrangement in which wells in adjacent rows are not offset from each other in a predetermined direction when a plurality of rows of the wells arrayed along the predetermined direction are disposed side by side so as to be adjacent to each other along a direction orthogonal to the predetermined direction.

While the length L2 of the diameter of each of the pillars 12d is substantially equal to the length L1 of the diameter of each of the wells 1 in the aforementioned embodiment, the present invention is not limited to this. For example, the length L2 of the diameter of each of the pillars 12d may be smaller than the length L1 of the diameter of each of the wells 1.

While only one inlet 12e of the gas flow path 12a is provided in the side surface 12g of the flow unit 12 in the aforementioned embodiment, the present invention is not limited to this. For example, a plurality of inlets 12e may be provided in the side surface 12g of the flow unit 12.

While each of the culturing unit 11, the flow unit 12, and the gas permeator 13 is made of silicone rubber in the aforementioned embodiment, the present invention is not limited to this. For example, each of the culturing unit 11, the flow unit 12, and the gas permeator 13 may be made of a material other than silicone rubber as long as the material is flexible and highly biocompatible. The gas permeator 13 needs to be oxygen permeable and liquid impermeable.

While the culturing unit 11, the flow unit 12, and the gas permeator 13 are integral and unitary with each other in the aforementioned embodiment, the present invention is not limited to this. For example, the culturing unit 11, the flow unit 12, and the gas permeator 13 may be separate from each other and may be made of materials different from each other.

While the culturing unit 11 is circumferentially wound and used in the aforementioned embodiment, the present invention is not limited to this. For example, the culturing unit 11 may be used in the form of a plate. In such an example, the culturing unit 11, the flow unit 12, and the gas permeator 13 do not have to be flexible.

While the pillars 12d are provided inside the gas flow path 12a in the aforementioned embodiment, the present invention is not limited to this. For example, the pillars 12d may not be provided as long as the required mechanical strength of the gas flow path 12a can be ensured.

While the gas permeator 13 is made of a material (silicone rubber) capable of transmitting oxygen in the aforementioned embodiment, the present invention is not limited to this. For example, the gas permeator may have minute holes through which gas passes but liquid does not pass, and oxygen may be transmitted (may pass) through the holes.

While the wells 1 are provided on the inner circumferential surface 11a (surface, circumferential surface) of the culturing unit 11 in the aforementioned embodiment, the present invention is not limited to this. For example, the wells 1 may be provided on the outer circumferential surface of the culturing unit 11.

While the inlet 12e has a substantially rectangular shape in the aforementioned embodiment, the present invention is not limited to this. For example, the inlet 12e may have a substantially elliptical shape.

What is claimed is:

1. A cell culture apparatus comprising:
    a culturing unit having a surface provided with a plurality of concave wells for culturing cells therein; and
    a flow unit provided on at least one of one side and the other side of the culturing unit in a direction orthogonal to the surface of the culturing unit, the flow unit including a gas flow path which allows gas to flow therethrough, and which extends along the surface and which is provided inside of the flow unit, wherein
    the culturing unit includes a gas permeator that is arranged to separate the plurality of concave wells of the culturing unit from the flow unit, the gas permeator having oxygen permeability and liquid impermeability, and
    the flow unit and the gas permeator are integral and unitary with each other.

2. The cell culture apparatus according to claim 1, wherein
    the culturing unit is flexible and circumferentially windable;
    the flow unit is flexible and circumferentially windable integrally with the culturing unit; and
    the gas permeator is arranged to separate each of the plurality of concave wells provided on at least one of an inner circumferential surface and an outer circumferential surface of the culturing unit from the flow unit in a state in which the culturing unit and the flow unit are integrally wound.

3. The cell culture apparatus according to claim 2, wherein the flow unit further includes a plurality of pillars that extend in a radial direction between a surface of the gas flow path on an inner circumferential side and a surface of the gas flow path on an outer circumferential side in the state in which the culturing unit and the flow unit are integrally wound.

4. The cell culture apparatus according to claim 3, wherein each of the plurality of pillars has a non-overlapping portion with the concave wells as viewed in the radial direction in the state in which the culturing unit and the flow unit are integrally wound.

5. The cell culture apparatus according to claim 4, wherein each of the pillars has a center located substantially at a midpoint between adjacent concave wells, as viewed in the radial direction.

6. The cell culture apparatus according to claim 4, wherein
    the plurality of concave wells are provided in a staggered manner on at least one of the inner circumferential surface and the outer circumferential surface of the culturing unit; and
    the plurality of pillars are provided in a staggered manner inside the gas flow path such that each of the plurality of pillars has a non-overlapping portion with the concave wells.

7. The cell culture apparatus according to claim 4, wherein
    each of the plurality of concave wells has a substantially cylindrical concave shape;
    each of the plurality of pillars has a substantially cylindrical shape; and
    a diameter of each of the pillars having the substantially cylindrical shape is equal to or less than a diameter of each of the concave wells having the substantially cylindrical concave shape.

8. The cell culture apparatus according to claim 1, wherein
    the flow unit has a substantially rectangular shape; and
    the gas flow path has an inlet provided in a side surface that extends along a short-side direction of the flow unit at an end of the flow unit on an outer diameter side in a state in which the culturing unit and the flow unit are integrally wound.

9. The cell culture apparatus according to claim 8, wherein the apparatus is configured to allow the gas supplied from a pump to flow into the inlet of the gas flow path.

10. The cell culture apparatus according to claim 1, wherein each of the culturing unit, the flow unit, and the gas permeator is made of silicone rubber.

11. The cell culture apparatus according to claim 1, wherein the culturing unit, the flow unit, and the gas permeator are integral and unitary with each other.

* * * * *